(12) United States Patent
Bisrat et al.

(10) Patent No.: US 9,314,525 B2
(45) Date of Patent: Apr. 19, 2016

(54) PICROPODOPHYLLIN POLYMORPH C AND ITS USE IN CANCER THERAPY

(75) Inventors: Mikael Bisrat, Strängnäs (SE); Magnus Brisander, Ekerö (SE)

(73) Assignee: Axelar AB, Solna (SE)

( * ) Notice: Subject to any disclaimer, the term of this patent is extended or adjusted under 35 U.S.C. 154(b) by 0 days.

(21) Appl. No.: 13/878,074

(22) PCT Filed: Oct. 7, 2011

(86) PCT No.: PCT/SE2011/051207
§ 371 (c)(1),
(2), (4) Date: Aug. 14, 2013

(87) PCT Pub. No.: WO2012/047171
PCT Pub. Date: Apr. 12, 2012

(65) Prior Publication Data
US 2013/0317099 A1   Nov. 28, 2013

Related U.S. Application Data

(60) Provisional application No. 61/391,114, filed on Oct. 8, 2010, provisional application No. 61/391,110, filed on Oct. 8, 2010, provisional application No. 61/410,014, filed on Nov. 4, 2010, provisional application No. 61/488,190, filed on May 20, 2011.

(51) Int. Cl.
*A61K 45/06* (2006.01)
*C07D 493/04* (2006.01)
*A61K 31/365* (2006.01)

(52) U.S. Cl.
CPC ............ *A61K 45/06* (2013.01); *A61K 31/365* (2013.01); *C07D 493/04* (2013.01)

(58) Field of Classification Search
CPC ..... A61K 31/365; A61K 45/06; C07D 493/04
USPC .......................................... 549/298; 514/463
See application file for complete search history.

(56) References Cited

U.S. PATENT DOCUMENTS

| 4,021,495 | A * | 5/1977 | Hosaka et al. ............. 568/742 |
| 2013/0245285 | A1 | 9/2013 | Axelsson et al. |
| 2013/0331445 | A1 | 12/2013 | Bisrat et al. |

FOREIGN PATENT DOCUMENTS

| CN | 101492704 | 7/2009 |
| GB | 1052917 | 12/1966 |
| WO | WO-02/102804 | 12/2002 |
| WO | WO-2004-055022 | 7/2004 |
| WO | WO-2009-157858 | 8/2007 |
| WO | WO-2007-097707 | 12/2009 |
| WO | WO-2012/047172 | 4/2012 |

OTHER PUBLICATIONS

Oxford English Dictionary,Copyright © 2013 Oxford University Press. p. 1.*
Andrews et al., "Asymmetric Total Synthesis of (—)-Podophyllotoxin," J. Am. Chem. Soc., 1988, pp. 7854-7858, vol. 110, No. 23.
Avdeef et al., "Miniaturization of Powder Dissolution Measurement and Estimation of Particle Size," Chemistry & Biodiversity, 2009, pp. 1796-1811, vol. 6.
Tsinman et al., "Powder Dissolution Method for Estimating Rotating Disk Intrinsic Dissolution Rates of Low Solubility Drugs," Pharmaceutical Research, Sep. 2009, pp. 2093-2100, vol. 26, No. 9.
Buchardt et al., "Thermal Chemistry of Podophyllotoxin in Ethanol and a Comparison of the Cytostatic Activity of the Thermolysis Products," Journal of Pharmaceutical Sciences, Nov. 1986, pp. 1076-1080, vol. 75, No. 11.
Drake et al., "Podophyllotoxin and Picropodophyllin. I. Their Reduction by Lithium Aluminum Hydride," J. Am. Chem. Soc., Jan. 1951, pp. 201-205, vol. 73.
Bacsik, "Comparison of Infrared Spectra of Picropodophyllin from Axelar AB and Literature Infrared Data," Expert Report, Stockholm University, Jun. 19, 2012, pp. 1-5.
Fagerberg et al., "Dissolution Rate and Apparent Solubility of Poorly Soluble Drugs in Biorelevant Dissolution Media," Molecular Pharmaceutics, 2010, pp. 1419-1430, vol. 7, No. 5.
Fonseca et al., "$^{13}$C NMR Analysis of Podophyllotoxin and Some of Its Derivatives," Phytochemistry, 1980, pp. 1527-1530, vol. 19.
Galia et al., "Evaluation of Various Dissolution Media for Predicting In Vivo Performance of Class I and II Drugs," Pharmaceutical Research, 1998, pp. 698-705, vol. 15, No. 5.
Gensler et al., "Compounds Related to Podophyllotoxin. X. Synthesis of Picropodophyllin," J. Am. Chem. Soc., Apr. 5, 1960, pp. 1714-1727, vol. 82.
Gensler et al., "Compounds Related to Podophyllotoxin. XII. Podophyllotoxone, Picropodophyllone and Dehydropodophyllotoxin," J. Am. Chem. Soc., Dec. 5, 1960, pp. 6074-6081, vol. 82.
Gensler et al., "The Podophyllotoxin-Picropodophyllin Equilibrium," J. Org. Chem., Oct. 1966, pp. 3224-3227, vol. 31.
International Search Report for PCT/SE2011/051208, mailed Jan. 11, 2012.
Jeong et al., "Lignans and Coumarins from the Roots of Anthriscus sylvestris and Their Increase of Caspase-3 Activity in HL-60 Cells," Bio. Pharm. Bull., 2007, pp. 1340-1343, vol. 30, No. 7.
Kurihara et al., "Studies of the Constituents of Diphylleia Grayi Fr. Schm.," Tohoku Yakka Daigaku Kiyo, 1961, pp. 111-114, vol. 8.
Liu et al., "A Study of the Chemical Components of *Podophyllum emdi* var. *Chinensis* Sprague," Acta Pharmaceutica Sinica, Apr. 1979, pp. 241-244, vol. 14, No. 4.
Chandramohan et al., "Crystal Structure of Picropodophyllin," Z. Kristallogr., 2000, pp. 45-47, vol. 215.
Hartwell et al., "Components of Podophyllin. V. The Constitution of Podophyllotoxin," J. Am. Chem. Soc., Jun. 1951, pp. 2909-2916, vol. 73.
Search Report by PRV InterPat, Jun. 1, 2011.

(Continued)

*Primary Examiner* — Samantha Shterengarts
*Assistant Examiner* — Matt Mauro
(74) *Attorney, Agent, or Firm* — White & Case LLP

(57) ABSTRACT

The invention relates to novel polymorphs of picropodophyllin, methods for preparing said polymorphs and pharmaceutical compositions comprising said polymorphs, as well as the use of said polymorphs in therapy such as cancer therapy.

20 Claims, 8 Drawing Sheets

(56) References Cited

OTHER PUBLICATIONS

"Picropodophylloxin," website printout from http://www.signmaaldrich.com/catalog/prodcut/sigma/t9576?LANG=en&region=GB, retrieved on Feb. 21, 2014.

Viehoever et al., "Biochemistry of May Apple Root (*Podophyllum Peltatum*) I.," J. Am. Pharm. Assoc., 1938, pp. 632-643, vol. 27, No. 8.

Wen et al., "Kinetic Investigation of Thermal Decomposition Reactions of Podophyllotoxin and Its Derivatives," Chinese Journal of Chemistry, 2006, pp. 29-36, vol. 24.

Written Opinion for PCT/SE2011/051208, mailed Jan. 11, 2012.

International Search Report for PCT/SE2011/051207, mailed Jan. 13, 2012.

Written Opinion for PCT/SE2011/051207, mailed Jan. 13, 2012.

Schrecker et al., "On the structure of Podophyllotoxin and the Peltatins," Helvetica Chimica Acta, 1954, vol. 37, No. 177, pp. 1541-1543.

Byrn et al., "Pharmaceutical Solids: A Strategic Approach to Regulatory Considerations," Pharm. Res., 1995, vol. 12, No. 7, pp. 945-954.

Borsche et al., "About podophyllin," Liebig. Ann. Chem., 1932, pp. 126-142.

Podwyssotzki, "Pharmacological Studies on Podophyllum peltatum," Arch. Exp. Pathol. Phar., 1880, pp. 29-52, vol. 13.

* cited by examiner

PICROPODOPHYLLIN POLYMORPH C AND ITS USE IN CANCER THERAPY

FIELD OF THE INVENTION

The present invention relates to novel polymorphs of picropodophyllin, to methods for their preparation, their use in therapy as well as pharmaceutical compositions comprising said polymorphs.

BACKGROUND OF THE INVENTION

Pharmaceutical solids can exist in different forms, such as crystalline, amorphous, or glass and also in solvated or hydrated forms. A polymorph is a solid crystalline phase of a compound resulting from the possibility of at least two crystalline arrangements of the molecules of that compound in the solid state.

It is a well known fact that different forms of the same drug may provide differences in certain pharmaceutically important physicochemical properties, such as stability, solubility, dissolution rate, crystal habit and tableting behavior. Changes in certain of these physiochemical properties may ultimately affect the bioavailability of the drug.

Picropodophyllin is a compound belonging to the class of compounds denominated cyclolignans, having the chemical structure:

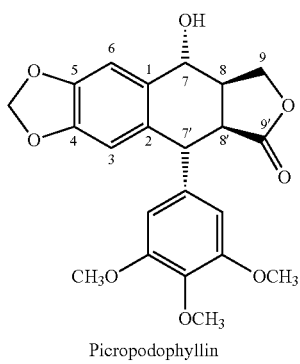

Picropodophyllin

For a long time, picropodophyllin attracted little interest, since it was believed to possess no or low biological activity. In contrast, its stereoisomer podophyllotoxin, which has a trans configuration in the lactone ring, has been studied for decades due to its cytotoxic properties.

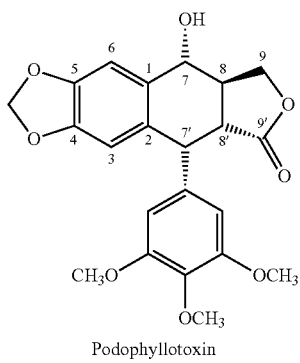

Podophyllotoxin

However, research has proven that picropodophyllin exhibits interesting biological properties and hence potential as a medicament.

WO 02/102804 discloses that picropodophyllin is a specific and potent inhibitor of insulin-like growth factor-1 receptor (IGF-1R) and may be useful in the treatment of IGF-1R dependent diseases such as various types of cancer, artheriosclerosis, psoriasis, and restenosis following coronary angioplasty.

WO 2007/097707 discloses the use of picropodophyllin in the prophylaxis or treatment of diabetes mellitus type 2, nephropathy, retinopathy, macular degeneration, retinopathy of prematurity, central retinal vein occlusion, branch retinal vein occlusion, rubeotic glaucoma, thyroid eye disease, corneal graft rejection and corneal chemical burns; and for contraception.

WO 2009/157858 discloses the use of picropodophyllin for the prophylaxis or treatment of diseases or conditions characterized by a hyperactive immune system such as rheumatoid arthritis, Crohn's disease, ulcerative colitis, multiple sclerosis, Alzheimer's disease, asthma, eczematous dermatitis, and graft rejection following transplantation.

Z. Kristallogr. 215 (2000) pp. 45-47 discloses a crystalline structure of picropodophyllin for which crystal data are reported.

Picropodophyllin monohydrate and picropodophyllin polymorph A are disclosed by Schrecker et al in Helvetica Chimica Acta (1954); 37; pp. 1541-1543.

DESCRIPTION OF THE INVENTION

Brief Description of the Accompanying Drawings

DETAILED DESCRIPTION

Figure 1:
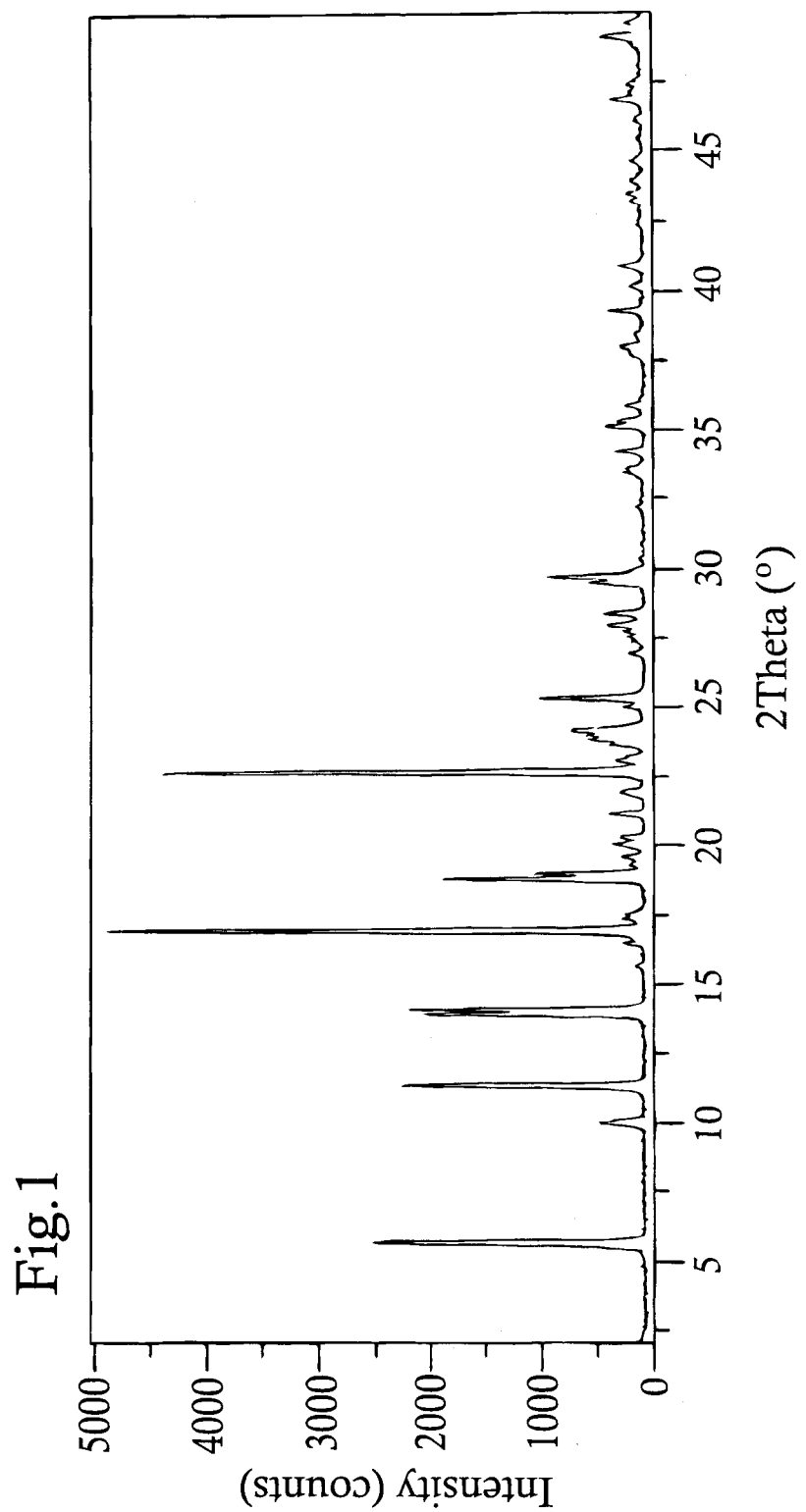
FIG. 1 is an X-ray powder diffractogram (XRPD) of picropodophyllin polymorph B measured on a zero background quartz single crystal specimen support.

An aspect of the present invention is to provide a novel polymorph of picropodophyllin.

An aspect of the invention is to provide a novel polymorph exhibiting low hygroscopicity.

Yet an aspect of the invention is to provide a novel and physically stable polymorph.

Still an aspect of the invention is to provide a novel polymorph showing good solubility.

The following definitions shall apply throughout the specification and the appended claims unless specifically stated otherwise:

Low hygroscopicity is herein defined as a mass increase equal to or less than 2%, such as equal to or less than 1%, after storage during 3 months at 40° C./75% RH and at 25° C./60% RH respectively. Low hygroscopicity facilitates handling and is advantageous from the perspectives of pharmaceutical manufacturing and storage stability.

Good solubility is herein defined as a solubility equal to or greater than that of picropodophyllin monohydrate, after stirring for 24 hours in 1% SDS in water, i.e. equal to or greater than 0.2 mg/ml.

Physically stable is herein defined as the form of the compound that is formed and which form continues to exist at ambient temperature, such as at a temperature from 20 to 25° C. or at a temperature from 25 to 120° C., at approximately 760 mmHg.

Diffraction and spectral data may be recorded for polymorphs using X-ray powder diffractometry (XRPD) and Infrared Spectroscopy (IR) respectively. It is to be understood that the sample preparation may influence the outcome of the measurement. Thus, XRPD pattern for the same polymorph may vary in respect of, for instance, peak positions and intensities depending on if the polymorph sample was measured on a zero background quartz single crystal specimen support or using a capillary as described hereinafter.

An aspect of the present invention is to provide picropodophyllin polymorph B.

Yet an aspect of the invention is to provide picropodophyllin polymorph B exhibiting low hygroscopicity.

Picropodophyllin polymorph B may be characterized as described hereinafter when measured on a zero background quartz single crystal specimen support.

In one aspect of the invention, there is provided picropodophyllin polymorph B characterized by having an X-ray powder diffraction pattern exhibiting a peak at 5.7±0.2° 2θ.

In one aspect of the invention, there is provided picropodophyllin polymorph B characterized by having an X-ray powder diffraction pattern exhibiting peaks at 5.7 and 10.0±0.2° 2θ.

Yet an aspect of the invention is picropodophyllin polymorph B characterized by having an X-ray powder diffraction pattern exhibiting peaks at 5.7, 10.0, 10.1 and 11.3±0.2° 2θ.

In one aspect of the invention, there is provided picropodophyllin polymorph B characterized by having an X-ray powder diffraction pattern exhibiting peaks at 5.7, 10.0, 10.1, 11.3, 13.9 and 14.1±0.2° 2θ.

Picropodophyllin polymorph B may be characterized as described hereinafter when measured using a capillary.

In one aspect of the invention, there is provided picropodophyllin polymorph B characterized by having an X-ray powder diffraction pattern exhibiting a peak at 5.6±0.2° 2θ.

In one aspect of the invention, there is provided picropodophyllin polymorph B characterized by having an X-ray powder diffraction pattern exhibiting peaks at 5.6 and 9.9±0.2° 2θ.

Yet an aspect of the invention is picropodophyllin polymorph B characterized by having an X-ray powder diffraction pattern exhibiting peaks at 5.6, 9.9, 10.0 and 11.2±0.2° 2θ.

In one aspect of the invention, there is provided picropodophyllin polymorph B characterized by having an X-ray powder diffraction pattern exhibiting peaks at 5.6, 9.9, 10.0, 11.2, 13.8 and 14.0±0.2° 2θ.

In one aspect of the invention, there is provided picropodophyllin polymorph B characterized by having an IR spectrum exhibiting a peak at 1736.9 cm$^{-1}$.

In one aspect of the invention, there is provided picropodophyllin polymorph B characterized by having an IR spectrum exhibiting peaks at 1736.9; 2841.5; 2936.0; 2970.9 and 3425.5 cm$^{-1}$.

In one aspect of the invention, there is provided picropodophyllin polymorph B characterized by having an IR spectrum exhibiting peaks at 1465.7; 1482.5; 1590.0; 1736.9; 2841.5; 2936.0; 2970.9; 3425.5 cm$^{-1}$.

In one aspect of the invention, there is provided picropodophyllin polymorph B characterized by having an IR spectrum exhibiting peaks at 1032.3; 1129.0; 1243.4; 1273.3; 1465.7; 1482.5; 1590.0; 1736.9; 2841.5; 2936.0; 2970.9 and 3425.5 cm$^{-1}$.

In one aspect of the invention, there is provided picropodophyllin polymorph B characterized by having an IR spectrum as described hereinbefore together with an XRPD pattern as described hereinbefore.

In one aspect of the invention there is provided picropodophyllin polymorph B exhibiting an XRPD pattern essentially as shown in FIG. 1.

Figure 2:
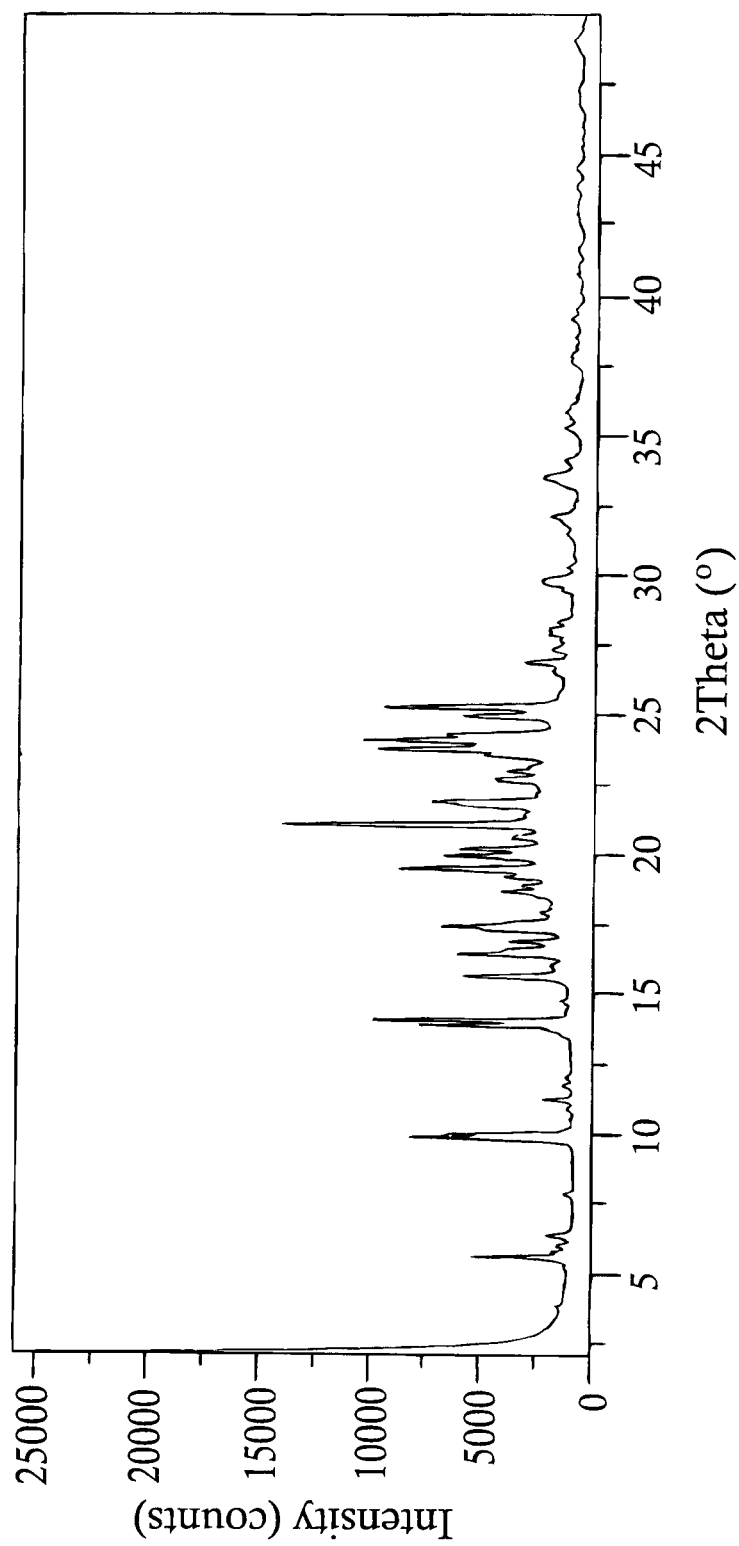
FIG. 2 is an X-ray powder diffractogram (XRPD) of picropodophyllin polymorph B measured in a capillary.

In one aspect of the invention there is provided picropodophyllin polymorph B exhibiting an XRPD pattern essentially as shown in FIG. 2.

Figure 5:
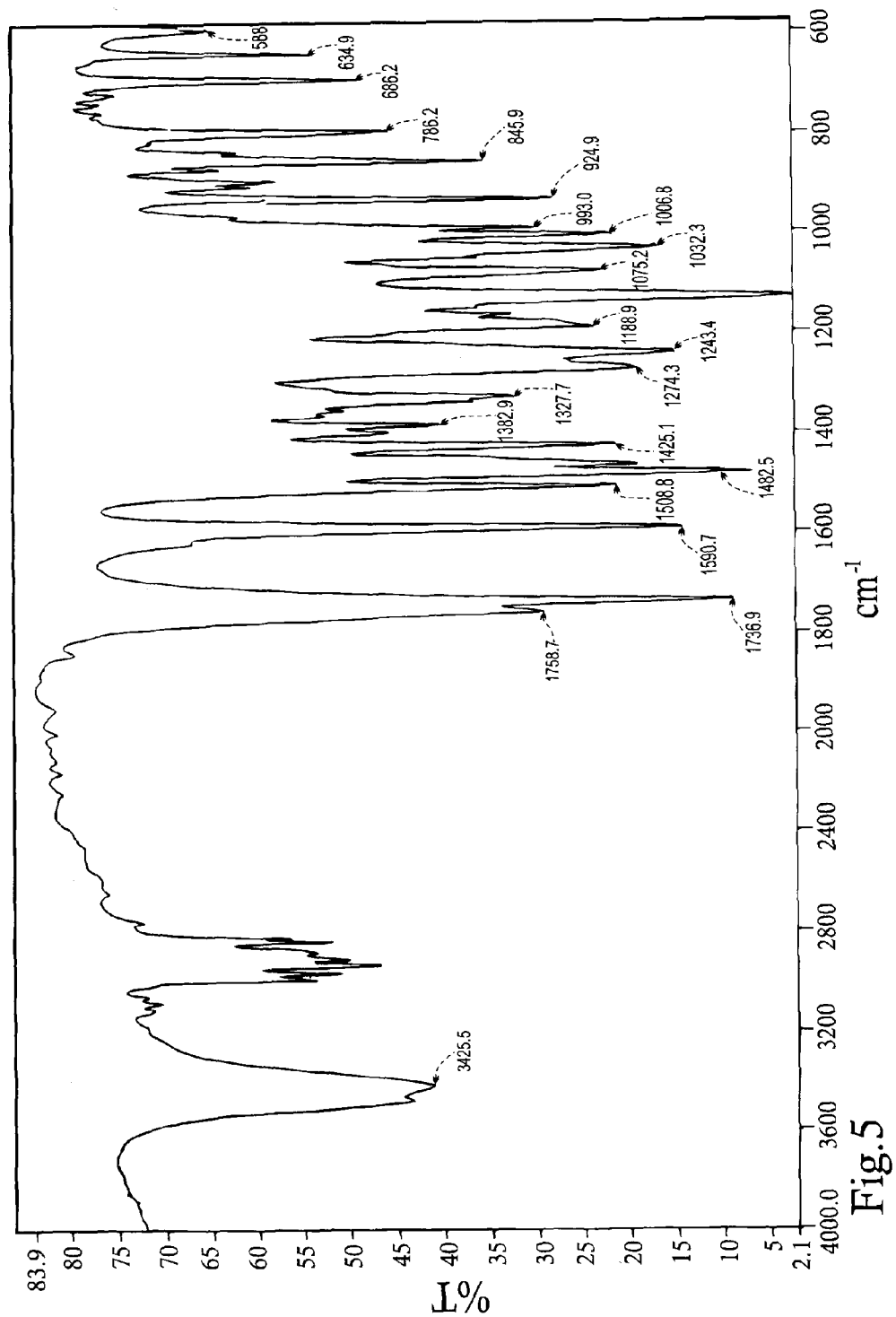
FIG. 5 is an infrared (IR) spectrum of picropodophyllin polymorph B.

In one aspect of the invention there is provided picropodophyllin polymorph B exhibiting an IR pattern essentially as shown in FIG. 5.

In one aspect of the invention there is provided picropodophyllin polymorph B exhibiting an XRPD pattern and an IR spectrum essentially as shown in FIG. 1 and in FIG. 5.

In one aspect of the invention there is provided picropodophyllin polymorph B exhibiting an XRPD pattern and an IR spectrum essentially as shown in FIG. 2 and in FIG. 5.

In a further aspect of the invention there is provided a method for transforming picropodophyllin polymorph B into picropodophyllin polymorph C, comprising the steps of:
  a) mixing picropodophyllin polymorph B with picropodophyllin polymorph C in a saturated solution of picropodophyllin in an organic solvent;
  b) stirring the mixture obtained in step a) to obtain a precipitate; and
  c) filtering off the thus obtained precipitate.

In a further aspect, there is provided a method as defined above in which the organic solvent is selected from acetone, ethyl acetate or mesitylene.

In a further aspect, there is provided a method as defined above in which at least one of the steps a), b) or c) is performed at room temperature, i.e. at a temperature from 20 to 25° C.

In a further aspect, there is provided a method as defined above in which at least one of the steps a), b) or c) is performed above room temperature, such as at a temperature of about 70° C. or at a temperature of about 120° C.

Yet an aspect of the invention, is a method for the preparation of picropodophyllin polymorph B as herein described, whereby picropodophyllin is recrystallized from a solvent selected from the group consisting of m-xylene, p-xylene, mesitylen, o-xylene anisol, isobutyl acetate, and a mixture thereof.

A further aspect of the present invention is to provide picropodophyllin polymorph C.

Yet an aspect of the invention, is a method for the preparation of picropodophyllin polymorph C as herein described, whereby picropodophyllin is recrystallized from a solvent selected from the group consisting of propionitrile, methyl ethyl ketone, n-butyl acetate, isobutylnitrile, butylformiate such as n-butylformiate or iso-butylformiate or tert-butylformiate, benzonitrile, cumene, dipropyl carbonate, and a mixture thereof.

Yet an aspect of the invention is to provide picropodophyllin polymorph C exhibiting low hygroscopicity.

Still an aspect of the invention is picropodophyllin polymorph C exhibiting physical stability at ambient temperature, such as at a temperature from 20 to 25° C., or at a temperature from 25 to 120° C., at approximately 760 mmHg.

Picropodophyllin polymorph C may be characterized as described hereinafter when measured on a zero background quartz single crystal specimen support.

In one aspect of the invention, there is provided picropodophyllin polymorph C characterized by having an X-ray powder diffraction pattern exhibiting a peak at 5.5±0.2° 2θ.

In one aspect of the invention, there is provided picropodophyllin polymorph C characterized by having an X-ray powder diffraction pattern exhibiting peaks at 5.5 and 7.0±0.2° 2θ.

In one aspect of the invention, there is provided picropodophyllin polymorph C characterized by having an X-ray diffraction powder pattern exhibiting peaks at 5.5, 7.0, 8.3 and 11.0±0.2° 2θ.

In one aspect of the invention, there is provided picropodophyllin polymorph C characterized by having an X-ray powder diffraction pattern exhibiting peaks at 5.5, 7.0, 8.3, 11.0, 11.6 and 11.8±0.2° 2θ.

Picropodophyllin polymorph C may be characterized as described hereinafter when measured in a capillary.

In one aspect of the invention, there is provided picropodophyllin polymorph C characterized by having an X-ray powder diffraction pattern exhibiting a peak at 5.4±0.2° 2θ.

In one aspect of the invention, there is provided picropodophyllin polymorph C characterized by having an X-ray powder diffraction pattern exhibiting peaks at 5.4 and 6.9±0.2° 2θ.

In one aspect of the invention, there is provided picropodophyllin polymorph C characterized by having an X-ray powder diffraction pattern exhibiting peaks at 5.4, 6.9, 8.2 and 9.7±0.2° 2θ.

In one aspect of the invention, there is provided picropodophyllin polymorph C characterized by having an X-ray powder diffraction pattern exhibiting peaks at 5.4, 6.9, 8.2, 9.7, 10.0 and 10.9±0.2° 2θ.

In one aspect of the invention, there is provided picropodophyllin polymorph C characterized by having an X-ray powder diffraction pattern exhibiting peaks at 5.4, 6.9, 8.2, 9.7, 10.0, 10.9, 11.5 and 11.7±0.2° 2θ.

In one aspect of the invention, there is provided picropodophyllin polymorph C characterized by having an IR spectrum exhibiting a peak at 1773.8 cm$^{-1}$.

In one aspect of the invention, there is provided picropodophyllin polymorph C characterized by having an IR spectrum exhibiting peaks at 1773.8; 2842.2; 2943.2; 2993.8 and 3436.0 cm$^{-1}$.

In one aspect of the invention, there is provided picropodophyllin polymorph C characterized by having an IR spectrum exhibiting peaks at 1425.8; 1462.5; 1479.0; 1592.8; 1773.8; 2842.2; 2943.2; 2993.8 and 3436.0 cm$^{-1}$.

In one aspect of the invention, there is provided picropodophyllin polymorph C characterized by having an IR spectrum exhibiting peaks at 1031.2; 1129.0; 1184.5; 1233.6; 1425.8; 1462.5; 1479.0; 1592.8; 1773.8; 2842.2; 2943.2; 2993.8 and 3436.0 cm$^{-1}$.

In one aspect of the invention, there is provided picropodophyllin polymorph C characterized by having an XRPD pattern and an IR spectrum as described hereinbefore.

Figure 3:
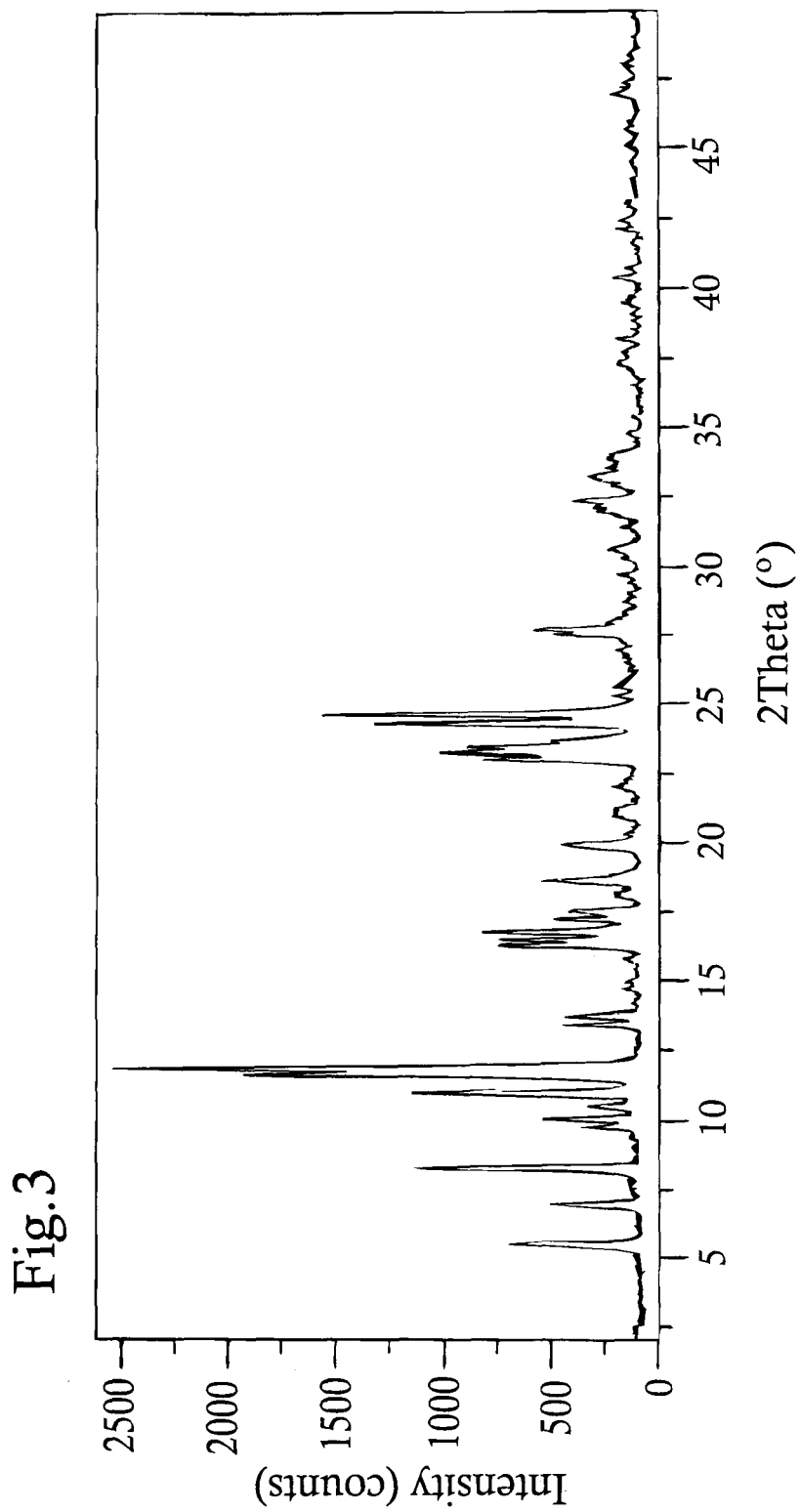
FIG. 3 is an X-ray powder diffractogram (XRPD) of picropodophyllin polymorph C measured on a zero background quartz single crystal specimen support.

In one aspect of the invention there is provided picropodophyllin polymorph C exhibiting an XRPD pattern essentially as shown in FIG. 3.

Figure 4:
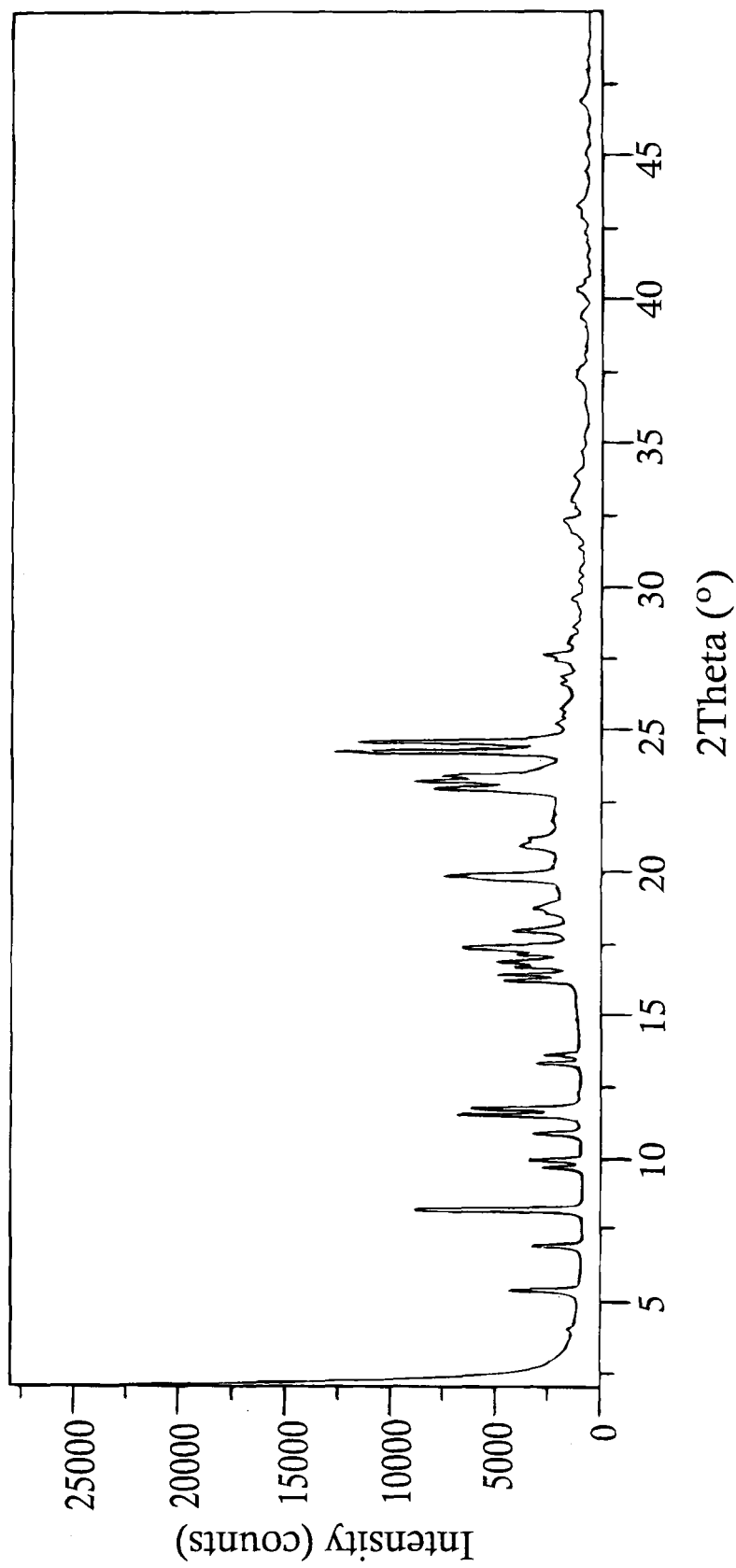
FIG. 4 is an X-ray powder diffractogram (XRPD) of picropodophyllin polymorph C measured in a capillary.

In one aspect of the invention there is provided picropodophyllin polymorph C exhibiting an XRPD pattern essentially as shown in FIG. 4.

Figure 6:
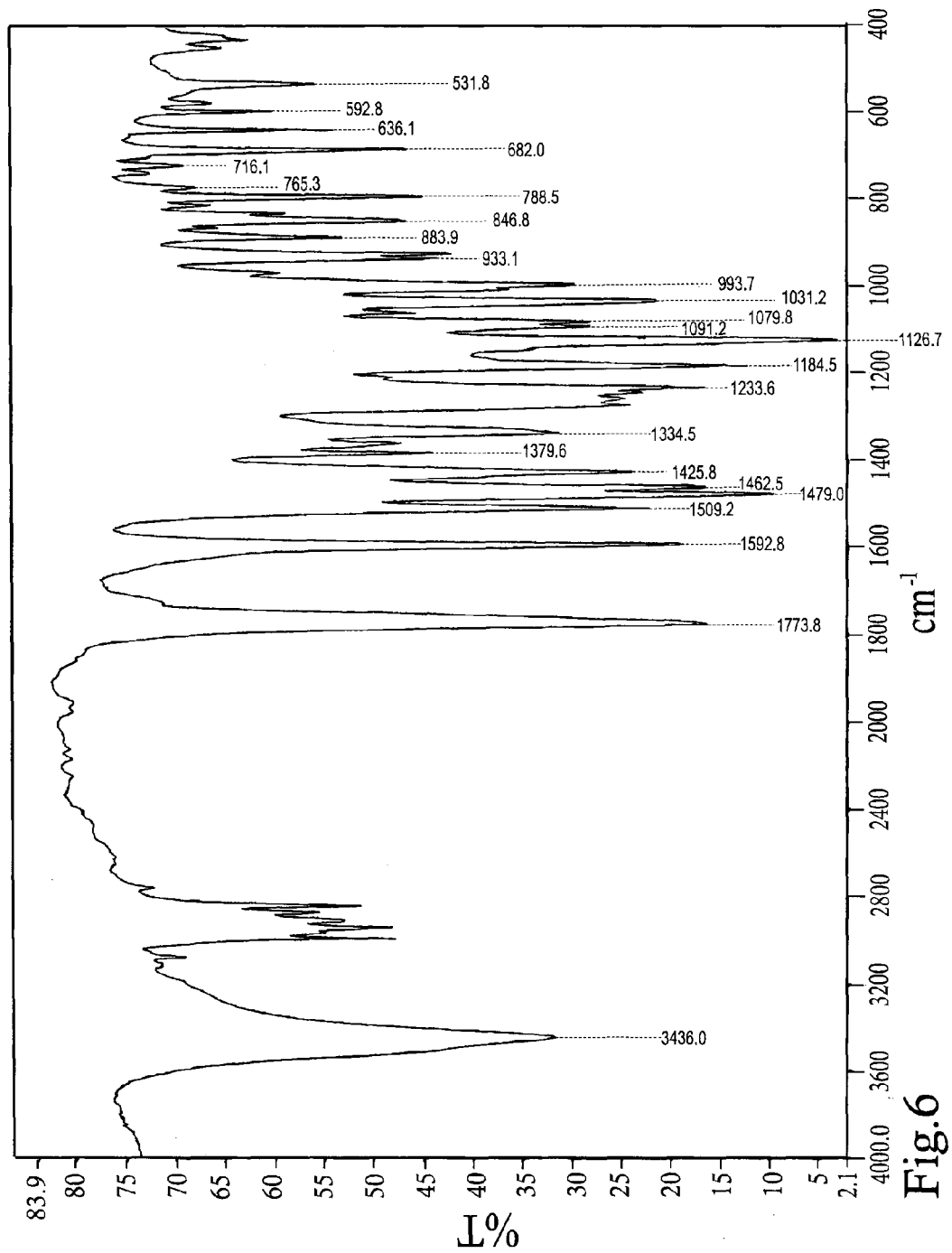
FIG. 6 is an infrared (IR) spectrum of picropodophyllin polymorph C.

In one aspect of the invention there is provided picropodophyllin polymorph C exhibiting an IR spectrum essentially as shown in FIG. 6.

In one aspect of the invention there is provided picropodophyllin polymorph C exhibiting an XRPD pattern and an IR spectrum essentially as shown in FIG. 3 and in FIG. 6, respectively.

In one aspect of the invention there is provided picropodophyllin polymorph C exhibiting an XRPD pattern and an IR spectrum essentially as shown in FIG. 4 and in FIG. 6, respectively.

One aspect of the invention is picropodophyllin polymorph B substantially free from any other polymorph and or any other crystal and for any other non-crystal form of picropodophyllin.

One aspect of the invention is picropodophyllin polymorph C substantially free from any other polymorph and/or any other crystal and/or any other non-crystal form of picropodophyllin.

The wording "substantially free from any other polymorph and/or any other crystal and/or any other non-crystal form of picropodophyllin" shall be understood to mean that picropodophyllin polymorph B contains less than 10%, such as less than 5%, or less than 1% of any other polymorph and/or any other crystal and/or any other non-crystal form of picropodophyllin.

The wording "substantially free from any other polymorph or any other crystal and/or any other non-crystal form of picropodophyllin" shall be understood to mean that picropodophyllin polymorph C contains less than 10%, such as less than 5%, or less than 1% of any other polymorph for any other crystal and/or any other non-crystal form of picropodophyllin.

In one aspect of the invention, there is provided picropodophyllin polymorph B for use in therapy.

In one aspect of the invention, there is provided picropodophyllin polymorph C for use in therapy.

Still an aspect of the invention, is the use of picropodophyllin polymorph B, for the manufacture of a medicament for the treatment of IGF-1R dependent diseases such as cancer.

Examples of cancer indications where picropodophyllin polymorph B as herein described may be useful, are lung cancer such as non-small cell lung cancer (NSCLC) or small cell lung cancer; breast cancer; head and neck cancer such as oral, sinusoidal or pharyngeal cancer; gastrointestinal cancer such as oesophageal cancer, stomach cancer, colon cancer, rectal cancer, gastrointestinal stromal tumor, liver cancer or pancreatic cancer; genitourinary cancer such as prostate cancer, bladder cancer or kidney cancer; gynecologic cancer such as ovarian cancer, cervical cancer, endometric cancer or uterine sarcoma; hematologic cancer such as myeloid leukemia, lymphocytic leukemia, lymphomas or multiple myeloma; musculoskeletal cancer such as Ewings sarcoma, osteosarcoma or soft tissue sarcoma; skin cancer such as malignant melanoma, basal cell cancer, squamous cell cancer or Kaposi's sarcoma; brain and neurologic cancer such as gliomas, glioblastoma, astrocytoma, medulloblastoma, craniopharyngeoma or neuroblastoma; endocrine cancer such as adrenocortical cancer, paraganglioma, pheochromocytoma or thyroid cancer; or eye cancer such as retinoblastoma or uveal melanoma.

Examples of non-small cell lung carcinoma (NSCLC) where picropodophyllin polymorph B as herein defined may be useful, are adenocarcinoma, squameous or large-cell carcinoma.

Yet an aspect of the invention is the use of picropodophyllin polymorph B, for the manufacture of a medicament for the treatment of psoriasis; restenosis after coronary angioplasty; diabetes mellitus type 2; nephropathy; eye diseases such as retinopathy or macular degeneration; rheumatoid arthritis; inflammatory bowel disease such as Crohns disease or ulcerative colitis; multiple sclerosis; Alzheimers disease; or graft rejection.

Still an aspect of the invention, is the use of picropodophyllin polymorph C, for the manufacture of a medicament for the treatment of IGF-1R dependent diseases such as cancer.

Examples of cancer indications where picropodophyllin polymorph C as herein described may be useful, are lung cancer such as non-small cell lung cancer (NSCLC) or small cell lung cancer; breast cancer; head and neck cancer such as oral, sinusoidal or pharyngeal cancer; gastrointestinal cancer such as oesophageal cancer, stomach cancer, colon cancer, rectal cancer, gastrointestinal stromal tumor, liver cancer or pancreatic cancer; genitourinary cancer such as prostate cancer, bladder cancer or kidney cancer; gynecologic cancer such as ovarian cancer, cervical cancer, endometric cancer or uterine sarcoma; hematologic cancer such as myeloid leukemia, lymphocytic leukemia, lymphomas or multiple myeloma; musculoskeletal cancer such as Ewings sarcoma, osteosarcoma or soft tissue sarcoma; skin cancer such as malignant melanoma, basal cell cancer, squamous cell cancer or Kaposi's sarcoma; brain and neurologic cancer such as gliomas, glioblastoma, astrocytoma, medulloblastoma, craniopharyngeoma or neuroblastoma; endocrine cancer such as adrenocortical cancer, paraganglioma, pheochromocytoma or thyroid cancer; or eye cancer such as retinoblastoma or uveal melanoma.

Examples of non-small cell lung carcinoma (NSCLC) where picropodophyllin polymorph C as herein defined may be useful, is adenocarcinoma, squameous or large-cell carcinoma.

Yet an aspect of the invention is the use of picropodophyllin polymorph C, for the manufacture of a medicament for the treatment of psoriasis; restenosis after coronary angioplasty; diabetes mellitus type 2; nephropathy; eye diseases such as retinopathy or macular degeneration; rheumatoid arthritis; inflammatory bowel disease such as Crohns disease or ulcerative colitis; multiple sclerosis; Alzheimers disease; or graft rejection.

Still an aspect of the invention, is picropodophyllin polymorph B for use in the treatment of IGF-1R dependent diseases such as cancer.

Examples of cancer indications where picropodophyllin polymorph B as herein described may be useful are lung cancer such as non-small cell lung cancer (NSCLC) or small cell lung cancer; breast cancer; head and neck cancer such as oral, sinusoidal or pharyngeal cancer; gastrointestinal cancer such as oesophageal cancer, stomach cancer, colon cancer, rectal cancer, gastrointestinal stromal tumor, liver cancer or pancreatic cancer; genitourinary cancer such as prostate cancer, bladder cancer or kidney cancer; gynecologic cancer such as ovarian cancer, cervical cancer, endometric cancer or uterine sarcoma; hematologic cancer such as myeloid leukemia, lymphocytic leukemia, lymphomas or multiple myeloma; musculoskeletal cancer such as Ewings sarcoma, osteosarcoma or soft tissue sarcoma; skin cancer such as malignant melanoma, basal cell cancer, squamous cell cancer or Kaposi's sarcoma; brain and neurologic cancer such as gliomas, glioblastoma, astrocytoma, medulloblastoma, craniopharyngeoma or neuroblastoma; endocrine cancer such as adrenocortical cancer, paraganglioma, pheochromocytoma or thyroid cancer; or eye cancer such as retinoblastoma or uveal melanoma.

Yet an aspect of the invention is picropodophyllin polymorph B for use in the treatment of psoriasis; restenosis after coronary angioplasty; diabetes mellitus type 2; nephropathy; eye diseases such as retinopathy or macular degeneration; rheumatoid arthritis; inflammatory bowel disease such as Crohns disease or ulcerative colitis; multiple sclerosis; Alzheimers disease; or graft rejection.

Still an aspect of the invention, is picropodophyllin polymorph C for use in the treatment of IGF-1R dependent diseases such as cancer.

Examples of cancer indications where picropodophyllin polymorph C as herein described may be useful are, lung cancer such as non-small cell lung cancer (NSCLC) or small cell lung cancer; breast cancer; head and neck cancer such as oral, sinusoidal or pharyngeal cancer; gastrointestinal cancer such as oesophageal cancer, stomach cancer, colon cancer, rectal cancer, gastrointestinal stromal tumor, liver cancer or pancreatic cancer; genitourinary cancer such as prostate cancer, bladder cancer or kidney cancer; gynecologic cancer such as ovarian cancer, cervical cancer, endometric cancer or uterine sarcoma; hematologic cancer such as myeloid leukemia, lymphocytic leukemia, lymphomas or multiple myeloma; musculoskeletal cancer such as Ewings sarcoma, osteosarcoma or soft tissue sarcoma; skin cancer such as malignant melanoma, basal cell cancer, squamous cell cancer or Kaposi's sarcoma; brain and neurologic cancer such as gliomas, glioblastoma, astrocytoma, medulloblastoma, craniopharyngeoma or neuroblastoma; endocrine cancer such as adrenocortical cancer, paraganglioma, pheochromocytoma or thyroid cancer; or eye cancer such as retinoblastoma or uveal melanoma.

Yet an aspect of the invention is picropodophyllin polymorph C for use in the treatment of psoriasis; restenosis after coronary angioplasty; diabetes mellitus type 2; nephropathy; eye diseases such as retinopathy or macular degeneration; rheumatoid arthritis; inflammatory bowel disease such as Crohns disease or ulcerative colitis; multiple sclerosis; Alzheimers disease; or graft rejection.

One aspect of the invention is a method for the treatment of IGF-1R dependent diseases such as cancer and more particularly for the treatment of lung cancer such as non-small cell lung cancer (NSCLC) or small cell lung cancer; breast cancer; head and neck cancer such as oral, sinusoidal or pharyngeal cancer; gastrointestinal cancer such as oesophageal cancer, stomach cancer, colon cancer, rectal cancer, gastrointestinal stromal tumor, liver cancer or pancreatic cancer; genitourinary cancer such as prostate cancer, bladder cancer or kidney cancer; gynecologic cancer such as ovarian cancer, cervical cancer, endometric cancer or uterine sarcoma; hematologic cancer such as myeloid leukemia, lymphocytic leukemia, lymphomas or multiple myeloma; musculoskeletal cancer such as Ewings sarcoma, osteosarcoma or soft tissue sarcoma; skin cancer such as malignant melanoma, basal cell cancer, squamous cell cancer or Kaposi's sarcoma; brain and neurologic cancer such as gliomas, glioblastoma, astrocytoma, medulloblastoma, craniopharyngeoma or neuroblastoma; endocrine cancer such as adrenocortical cancer, paraganglioma, pheochromocytoma or thyroid cancer; or eye cancer such as retinoblastoma or uveal melanoma; whereby a therapeutically effective amount of picropodophyllin polymorph B, is administered to a patient in need of such treatment.

Yet an aspect of the invention is a method for the treatment of psoriasis; restenosis after coronary angioplasty; diabetes mellitus type 2; nephropathy; eye diseases such as retinopathy or macular degeneration; rheumatoid arthritis; inflammatory bowel disease such as Crohns disease or ulcerative colitis; multiple sclerosis; Alzheimers disease; or graft rejection; whereby a therapeutically effective amount of picropodophyllin polymorph B is administered to a patient in need of such treatment.

One aspect of the invention is a method for the treatment of IGF-1R dependent diseases such as cancer and more particularly for the treatment of lung cancer such as non-small cell lung cancer (NSCLC) or small cell lung cancer; breast cancer; head and neck cancer such as oral, sinusoidal or pharyngeal cancer; gastrointestinal cancer such as oesophageal cancer, stomach cancer, colon cancer, rectal cancer, gastrointestinal stromal tumor, liver cancer or pancreatic cancer; genitourinary cancer such as prostate cancer, bladder cancer or kidney cancer; gynecologic cancer such as ovarian cancer, cervical cancer, endometric cancer or uterine sarcoma; hematologic cancer such as myeloid leukemia, lymphocytic leukemia, lymphomas or multiple myeloma; musculoskeletal cancer such as Ewings sarcoma, osteosarcoma or soft tissue sarcoma; skin cancer such as malignant melanoma, basal cell cancer, squamous cell cancer or Kaposi's sarcoma; brain and neurologic cancer such as gliomas, glioblastoma, astrocytoma, medulloblastoma, craniopharyngeoma or neuroblastoma; endocrine cancer such as adrenocortical cancer, paraganglioma, pheochromocytoma or thyroid cancer; or eye cancer such as retinoblastoma or uveal melanoma; whereby a therapeutically effective amount of picropodophyllin polymorph C is administered to a patient in need of such treatment.

Examples of non-small cell lung carcinoma (NSCLC) where picropodophyllin polymorph C as herein defined may be useful, is adenocarcinoma, squameous or large-cell carcinoma.

Yet an aspect of the invention is a method for the treatment of psoriasis; restenosis after coronary angioplasty; diabetes mellitus type 2; nephropathy; eye diseases such as retinopathy or macular degeneration; rheumatoid arthritis; inflammatory bowel disease such as Crohns disease or ulcerative colitis; multiple sclerosis; Alzheimers disease; or graft rejection; whereby a therapeutically effective amount of picropodophyllin polymorph C is administered to a patient in need of such treatment.

In one aspect of the invention, there is provided a pharmaceutical composition comprising picropodophyllin polymorph B in admixture with a pharmaceutically acceptable adjuvant, diluent and/or carrier.

In one aspect of the invention, there is provided a pharmaceutical composition comprising picropodophyllin polymorph C in admixture with a pharmaceutically acceptable adjuvant, diluent and/or carrier.

In one aspect of the invention, there is provided a kit of parts comprising:
(i) picropodophyllin polymorph B; and
(ii) an anti-cancer drug;
for sequential, separate or simultaneous administration.

In one aspect of the invention, there is provided a kit of parts comprising:
(i) picropodophyllin polymorph C; and
(ii) an anti-cancer drug;
for sequential, separate or simultaneous administration.

In one aspect of the invention, there is provided a kit of parts as herein described, for use in therapy.

Yet an aspect of the invention is a kit of parts as herein described, for the treatment of cancer such as lung cancer such as non-small cell lung cancer (NSCLC) or small cell lung cancer; breast cancer; head and neck cancer such as oral, sinusoidal or pharyngeal cancer; gastrointestinal cancer such as oesophageal cancer, stomach cancer, colon cancer, rectal cancer, gastrointestinal stromal tumor, liver cancer or pancreatic cancer; genitourinary cancer such as prostate cancer, bladder cancer or kidney cancer; gynecologic cancer such as ovarian cancer, cervical cancer, endometric cancer or uterine sarcoma; hematologic cancer such as myeloid leukemia, lymphocytic leukemia, lymphomas or multiple myeloma; musculoskeletal cancer such as Ewings sarcoma, osteosarcoma or soft tissue sarcoma; skin cancer such as malignant melanoma, basal cell cancer, squamous cell cancer or Kaposi's sarcoma; brain and neurologic cancer such as gliomas, glioblastoma, astrocytoma, medulloblastoma, craniopharyngeoma or neuroblastoma; endocrine cancer such as adrenocortical cancer, paraganglioma, pheochromocytoma or thyroid cancer; or eye cancer such as retinoblastoma or uveal melanoma.

Picropodophyllin polymorph B or picropodophyllin polymorph C as herein described may be administered via the oral, parenteral, intravenous, intramuscular, subcutaneous or by injectable administration routes, buccal, rectal, vaginal, transdermal, nasal or ophtalmic route, or via inhalation in the form of pharmaceutical compositions comprising a pharmaceutically acceptable dosage form. Depending upon the disorder and patient to be treated and the route of administration, the compositions may be administered at varying doses. In one aspect of the invention, polymorph B or polymorph C as herein described, is present in an amount of 1-95% by weight of the total weight of the pharmaceutical composition.

An aspect of the present invention is a pharmaceutical composition comprising polymorph B or polymorph C as herein described, in admixture with a pharmaceutically and pharmacologically acceptable adjuvant and/or carrier. The pharmaceutically and pharmacologically acceptable carrier suitable for a particular pharmaceutical composition will be apparent to a person skilled in the art of pharmaceutical compositions. The pharmaceutical composition may be administered to a subject or patient by an administration route suitable for the type of cancer or medical indication to be treated. For parenteral administration, polymorph B or polymorph C as herein described, may be administered as an injectable dosage form, or by continuos infusion, or as a suspension, said composition comprising polymorph B or polymorph C as herein described.

For oral administration, polymorph B or polymorph C as herein described, may be administered as a solid pharmaceutical composition, such as a capsule, a tablet, a pill, or as a powder.

In one aspect of the present invention, the dosage of polymorph B or polymorph C as herein described, may range from 1-40 mg/kg body weight per day.

In one aspect of the present invention, polymorph B or polymorph C as herein described, is administered in a dosage of 400 mg twice daily.

In yet an aspect of the present invention, polymorph B or polymorph C as herein described, is administered in a dosage of 390 mg twice daily.

Still an aspect of the invention is a combination of at least one anti-cancer drug and picropodophyllin polymorph B as herein described.

Still an aspect of the invention is a combination of at least one anti-cancer drug and picropodophyllin polymorph C as herein described.

Examples of anti-cancer drugs useful in combination with picropodophyllin polymorph B or picropodophyllin polymorph C as herein described are cytostatics; targeted anticancer agents being monoclonal antibodies or selective small-molecule inhibitors; hormones; antihormones; or immunostimulating agents.

Examples of cytostatics useful in combination therapy with picropodophyllin polymorph B or picropodophyllin polymorph C, as herein described, are alkylating agents such as melphalan; antimetabolites such as methotrexate or gemcitabine; mitotic inhibitors such as taxanes orvinca alkaloids; cytotoxic antibiotics such as doxorubicin; topoisomerase II inhibitors such as etoposide; or other cytostatics such as cisplatin or carboplatin.

Examples of monoclonal antibodies useful in combination therapy with picropodophyllin polymorph B or picropodophyllin polymorph C, as herein described, are those targeting the epidermal growth factor receptor (EGFR), HER2, and vascular endothelial growth factor such as trastozumab or bevacizumab.

Examples of selective small-molecule inhibitors useful in combination therapy with picropodophyllin polymorph B or picropodophyllin polymorph C, as herein described, are those targeting epidermal growth factor receptor, histone deacetylase (HDAC), Raf, platelet-derived growth factor receptors, vascular endothelial growth factor receptor, or c-Kit, such as gefitinib and imatinib.

Examples of hormones useful in combination therapy with picropodophyllin polymorph B or picropodophyllin polymorph C, as herein described, are estrogens or gestagens.

Examples of antihormones useful in combination therapy with picropodophyllin polymorph B or picropodophyllin polymorph C, as herein described, are antiestrogens, antiandrogens or enzyme inhibitors.

Examples of immunostimulating agents useful in combination therapy with picropodophyllin polymorph B or picropodophyllin polymorph C, as herein described, are interferons.

Methods of Preparation

In one aspect of the invention, there is provided a method for the preparation of picropodophyllin polymorph B as herein defined, whereby picropodophyllin in amorphous form is recrystallized from a solvent selected from m-xylene, p-xylene, mesitylen, anisol, isobutyl acetate, or a mixture thereof.

In one aspect of the invention, there is provided a method for the preparation of picropodophyllin polymorph B as herein defined, whereby picropodophyllin in crystalline form is recrystallized from a solvent selected from m-xylene, p-xylene, mesitylen, anisol, isobutyl acetate, or a mixture thereof.

In one aspect of the invention there is provided a method for the preparation of picropodophyllin polymorph B as herein defined, whereby picropodophyllin monohydrate is recrystallized from a solvent selected from m-xylene, p-xylene, mesitylen, anisol, isobutyl acetate, or a mixture of o-xylene, m-xylene, p-xylene, or a mixture thereof.

In one aspect of the invention, there is provided a method for the preparation of picropodophyllin polymorph C as herein defined, whereby picropodophyllin in amorphous form is recrystallized from a solvent selected from of propionitrile, methyl ethyl ketone, n-butyl acetate, isobutylnitrile, butylformiate such as n-butylformiate or iso-butylformiate or tert-butylformiate, benzonitrile, cumene, dipropyl carbonate, or a mixture thereof.

In one aspect of the invention, there is provided a method for the preparation of picropodophyllin polymorph C as herein defined, whereby picropodophyllin in crystalline form is recrystallized from a solvent selected from propionitrile, methyl ethyl ketone, n-butyl acetate, isobutylnitrile, butylformiate such as n-butylformiate or iso-butylformiate or tert-butylformiate, benzonitrile, cumene, dipropyl carbonate, or a mixture thereof.

In one aspect of the invention, there is provided a method for the preparation of picropodophyllin polymorph C as herein defined, whereby picropodophyllin monohydrate is recrystallized from a solvent selected from propionitrile, methyl ethyl ketone, n-butyl acetate, isobutylnitrile, butylformiate such as n-butylformiate or iso-butylformiate or tert-butylformiate, benzonitrile, cumene, dipropyl carbonate, or a mixture thereof.

The starting material picropodophyllin monohydrate was obtained as described in Example 1 hereinafter.

ABBREVIATIONS g gram(s)
DVS Dynamic Vapor Sorption
DSC Differential Scanning calorimetry
IR Infrared
LC Liquid Chromatography
LC UV Liquid Chromatography with UV detection
ml milliliter
L Liter
PVDF Polyvinylidene fluoride
RH Relative Humidity
SDS Sodium Dodecyl Sulfate
XRPD X-Ray Powder Diffraction
% T % Transmittance
TM Trade Mark
rpm Revolutions Per Minute
UV Ultraviolet
PhB Phosphate buffer
FeSSIF Fed state simulated intestinal fluid
IDR Intrinsic Dissolution Rate

EXAMPLES

X-Ray Powder Diffraction (XRPD) Using a Zero Background Quartz Single Crystal Specimen Support X-Ray Powder Diffraction (XRPD) experiments were run on an X'Pert Pro diffractometer (PANanalytical B.V., Netherlands) set in Bragg-Brentano geometry. The diffractometer was equipped with a Ge(111) primary monochromator and PIXcell detector. A representative sample was placed on a zero background quartz single crystal specimen support (Siltronix, France).

Experiments were run using Cu $K_{\alpha 1}$ radiation (45 kV and 40 mA) at ambient temperature and humidity. Scans were run in continues scan mode in the range 2-50° 2θ using automatic divergence and antiscatter slits with observed length of 10 mm, a step size of 0.0131° 2θ and a common counting time of 217.770 seconds. The sample was spun with a rotation time of 2 seconds.

It will be understood by a person skilled in the art that the 2-theta degree values of the X-ray powder diffraction pattern may vary slightly from one machine to another. Some variation may also exist due to sample preparation and variations between batches.

Data collections were done with the application software X'Pert Data Collector version 2.2d and instrument control software version 1.9D, and pattern analysis and profile refinement was done with X'Pert HighScore Plus version 2.2.3. All software's comes from PANanalytical B.V., Netherlands.

X-Ray Powder Diffraction (XRPD) Using a Capillary

X-Ray Powder Diffraction (XRPD) experiments were run on an X'Pert Pro multipurpose diffractometer with radius 240.0 mm (PANanalytical, Netherlands) set in capillary spinner configuration. The diffractometer was equipped with a 55.3 mm beam Cu W/Si mirror and an X'Celerator real time multi strip detector with an active length of 2.122° 2θ. A representative sample was placed in a quartz capillary with a length of 80 mm, outer diameter of 1.0 mm and wall thickness of 0.01 mm (Hampton research, U.S.A.).

Experiments were run using Cu $K_\alpha$ radiation (45 kV and 40 mA) at ambient temperature and humidity. Scans were run in continues scan mode in the range 2-50° 2θ with a step size of 0.0167° 2θ and a counting time of 151.765 seconds. The incident beam path contained a soller slit with 0.02 rad opening, a fixed mask with a width of 20.00 mm and fixed anti-scatter and divergence slits with a height of 0.76 mm. The diffracted beam path contained a fixed anti-scatter slit for capillary and transmission applications with a height of 2.5 mm and a soller slit with 0.02 rad opening.

It will be understood by a person skilled in the art, that the 2-theta degree values of the X-ray powder diffraction pattern may vary slightly from one machine to another. Some variation may also exist due to sample preparation and variations between batches.

Data collections were done with the application software X'Pert Data Collector version 2.2h and instrument control software version 2.0A, and pattern analysis was done X'Pert HighScore Plus version 2.2c. All softwares comes from PANanalytical, Netherlands.

Infrared Spectroscopy (IR)

IR spectra were recorded on a Perkin Elmer 2000 FTIR spectrometer starting at 4000 cm$^{-1}$ and ending at 400 cm$^{-1}$. The resolution was 4 cm$^{-1}$. The IR samples were prepared by mixing approximately 1 mg of picropodophyllin polymorph B or picropodophyllin polymorph C with approximately 300 mg of KBR and making a tablet thereof.

Example 1

Preparation of Picropodophyllin Monohydrate 17.3 kg (127 moles) of NaOAc×3H$_2$O was dissolved in water, filtered and added to a filtered solution of 10.5 kg (25 moles) of picropodophyllin in ethanol (95% in water, 198 L). The reaction mixture was kept at 70-75° C. during at least 2 hours, after which it was cooled. The product picropodophyllin was isolated through a Nutch filter, washed with ethanol (approximately 50% in water) and dried under vacuum. The thus obtained product was subjected to conditioning with water, i.e. the product was stored next to a beaker filled with water, during at least 96 hours to yield picropodophyllin monohydrate (8 kg).

Example 2

Crystallization of Picropodophyllin Polymorph B 0.503 g of picropodophyllin monohydrate obtained in Example 1 was dissolved in 45.0 ml p-xylene at reflux. The solution was removed from the heating plate, placed at 80° C. for one hour and thereafter at room temperature for additionally five hours. The crystals were filtered off and dried under vacuum overnight to give 0.310 g (yield 64.3%) of picropodophyllin polymorph B.

Picropodophyllin polymorph B was subsequently synthesized on a larger scale as follows: Picropodophyllin (20 g, monohydrate) was dissolved in p-xylene (1.9 L) at reflux. The solution was concentrated by evaporation of the solvent (about 1.1 L) at the boiling temperature. The product started to crystallize during evaporation and thin slurry was obtained. The slurry was removed from the heating bath and let cool down slowly to room temperature. More crystalline precipitate was obtained and the slurry became thicker. The slurry was equilibrated over night at room temperature. The crystals were then filtered off and dried on the filter at room temperature and atmospheric pressure in 3 days.

The water content was determined using the Karl Fischer method on a KF-1 instrument according to the method AM/General/water content as follows. The sample was heated to 150° C. for 600 s. The liberated gas (water) reacted with the titrant (hydranal). When the endpoint of the chemical reaction was reached, the amount of titrant used was converted to result in %. Water by Karl-Fischer: 0.2%.

Yield: 18.3 g (95.6%).

XRPD Peak Positions for Picropodophyllin Polymorph B

XRPD for Picropodophyllin Polymorph B Measured on a Zero Background Quartz Single Crystal Specimen Support:

Refined 2θ values:
5.7±0.2° 2θ
10.0±0.2° 2θ
10.1±0.2° 2θ
11.3±0.2° 2θ
13.9±0.2° 2θ
14.1±0.2° 2θ

XRPD for Picropodophyllin Polymorph B Using a Capillary:

Refined 2θ values:
5.6±0.2° 2θ
9.9±0.2° 2θ
10.0±0.2° 2θ
11.2±0.2° 2θ
13.8±0.2° 2θ
14.0±0.2° 2θ

Example 3

Crystallization of Picropodophyllin Polymorph C 0.502 g of picropodophyllin monohydrate obtained in Example 1, was dissolved in 13.0 ml methyl ethyl ketone (MEK) at reflux, thereafter the temperate of the solution was decreased to 70° C. and kept at this temperature for 30 minutes. The temperature was thereafter gradually decreased in 10° C. steps to 30° C. during two hours and thereafter kept at ambient temperature for additionally two hours. The crystals were filtered off and dried in open air overnight to give 0.230 g (yield 47.8%) of picropodophyllin polymorph C.

Picropodophyllin polymorph C was subsequently synthesized on a larger scale as follows: Picropodophyllin (22 g, monohydrate) was dissolved in methyl ethyl ketone (760 mL) at reflux. The solution was concentrated by evaporation of the solvent (about 200 mL) at the boiling temperature. The temperature of the solution was decreased to 55° C. and kept at this temperature in 30 minutes. The product started to crystallize. Thereafter the temperature was decreased to 40° C. A thick slurry was obtained, which was difficult to handle. The temperature was increased to 50° C. and kept at this temperature for 1 hour. The slurry became less thick. The temperature was then slowly decreased to room temperature and left for equilibration over night. Thereafter additional methyl ethyl ketone was evaporated at reduced pressure and the slurry was left for equilibration for 4 hours. The crystals were finally filtered off and dried on the filter at room temperature and atmospheric pressure for 2 days.

The water content was determined using the Karl Fischer method described above. Water by Karl-Fischer: 0.1%.

Yield: 16.4 g (77%)

XRPD Peak Positions for Picropodophyllin Polymorph C
XRPD for Picropodophyllin Polymorph C Measured on a Zero Background Quartz Single Crystal Specimen Support:
Refined 2θ values:
5.5±0.2° 2θ
7.0±0.2° 2θ
8.3±0.2° 2θ
11.0±0.2° 2θ
11.6±0.2° 2θ
11.8±0.2° 2θ

XRPD for Picropodophyllin Polymorph C Using a Capillary:
Refined 2θ values:
5.4±0.2° 2θ
6.9±0.2° 2θ
8.2±0.2° 2θ
9.7±0.2° 2θ
10.0±0.2° 2θ
10.9±0.2° 2θ
11.5±0.2° 2θ
11.7±0.2° 2θ

Example 4

Stability Studies

Polymorph B Stirred in Water

Approximately 27 mg polymorph B and 2 ml water was rotated for 24 hours. The slurry was centrifuged and the supernatant was removed. The solid was dried under vacuum overnight and the sample was thereafter, stored at ambient conditions.

XRPD analysis indicated that polymorph B stirred in water for 24 hours converted to a mixture of mainly picropodophyllin monohydrate and some picropodophyllin polymorph B.

Polymorph C Stirred in Water

A slurry of approximately 60 mg polymorph C and 2 ml purified water was rotated for 24 hours. The slurry was centrifuged and the supernatant was removed. The solid was dried under vacuum overnight and the sample was thereafter, stored at ambient conditions.

Polymorph C Sonicated for 5 Minutes 105 mg of polymorph C in 15.0 ml purified water was cooled on ice and sonicated for 5 minutes using a Sonicator XL Misonix, pulse sonication with gain 2. The slurry was centrifuged 3000 rpm for 10 minutes and the supernatant was removed. The solid was freezed (in a freezer) and freeze-dried overnight. The sample was kept at ambient conditions for 2 hours before the XRPD analysis.

Polymorph C Mortared for 5 Minutes

Approximately 50 mg polymorph C was mortared for 5 minutes in an agate mortar.

As indicated by XRPD no phase change occurred when picropodophyllin polymorph C was (a) dispersed in water and rotated for 24 hours (b) sonicated for 5 minutes or (c) mortared for 5 minutes.

Slurry Experiments with Polymorphs B and C at Ambient Temperature

Approximately 50 mg of polymorph C was stirred in 5.0 ml acetone, ethyl acetate and mesitylene, respectively overnight at ambient conditions. The solid was filtered off and the saturated picropodophyllin solutions were used in the slurry experiment below.

Mixture of Polymorphs B and C Stirred in Acetone

A slurry of 15.3 mg polymorph B and 15.0 mg polymorph C was stirred in 3.0 ml acetone saturated with picropodophyllin (see above) under five days at ambient conditions. The solid was filtered off using a glass filter and stored at ambient conditions for 2 hours.

Mixture of Polymorphs B and C Stirred in Ethyl Acetate

A slurry of 15.2 mg polymorph B and 15.1 mg polymorph C was stirred in 3.0 ml ethyl acetate saturated with picropodophyllin (see above) under five days at ambient conditions. The solid was filtered off using a glass filter and left on the glass filter for 30 minutes.

Mixture of Polymorphs B and C Stirred in Mesitylene

A slurry of 16.0 mg polymorph B and 15.5 mg polymorph C was stirred in 3.0 ml mesitylene saturated with picropodophyllin (see above) under five days at ambient conditions. The solid was filtered off using a glass filter and left on the glass filter for 30 minutes.

Slurry Experiments with Polymorphs B and C at 70° C. And 120° C.

Mixture of Polymorphs B and C Stirred in Mesitylene at 70° C.

Approximately 40 mg of polymorph C was stirred in 4.0 ml mesitylene at 70° C. for 1 hour. The solid was filtered off and 3.0 ml of the saturated picropodophyllin solution was added to 15.3 mg polymorph B and 15.0 mg polymorph C at 70° C. The slurry was slowly stirred overnight. The slurry was removed from the oil bath and immediately filtered through a glass filter. The solid was left on the glass filter for 30 minutes.

Mixture of Polymorphs B and C Stirred in Mesitylene at 120° C.

Approximately 40 mg of polymorph C was stirred in 4.0 ml mesitylene at 120° C. for 1 hour. The solid was filtered off and 3.0 ml of the saturated picropodophyllin solution was added to 15.2 polymorph B and 15.6 mg polymorph C at 120° C. The slurry was slowly stirred for 4 hours. The slurry was removed from the oil bath and immediately filtered through a glass filter. The solid was left on the glass filter for 30 minutes.

Slurry experiments with a mixture of polymorph B and polymorph C stirred in acetone, ethyl acetate and mesitylene, respectively, at ambient temperature provided polymorph C, i.e. polymorph B converted to polymorph C under the specified conditions.

Slurry experiments with a mixture of polymorph B and polymorph C in mesitylene at 70° C. and 120° C. gave polymorph C, i.e. polymorph B converted to polymorph C under the specified conditions.

Example 5

Solubility Studies

The solubility was determined in triplicate by use of LC-UV chromatography. An excess amount of substance (i.e. picropodophyllin polymorph B or picropodophyllin polymorph C) was weighed in vials and 0.5 ml of 1% SDS in water as added. The substance was rotated in the specific medium at ambient temperature for 24 hours, followed by filtering the supernatant using a hydrophilic PVDF (Millipore Corp.) 0.22 μm filter. The samples were then diluted with a 1:1 mixture of mobile phase A and B (see below) and analyzed using an Xterra™ MS $C_{18}$, 50×2.1 mm column with UV detection at 288 nm. The mobile phase consisted of acetonitrile, water and trifluoroacetic acid, 5:95:0.1 (A) and 99:1:0.1 (B). The gradient profile was: 0-3 minutes with a linear increase of mobile phase B from 20% to 100% followed by 2 minutes with 100% B. The solubility was calculated from a calibration curve with accurately weighed amounts of the substance, dissolved and diluted to different concentrations with a 1:1 mixture of mobile phase A and B.

Solubility determinations were performed in 1% sodium dodecyl sulfate (SDS) in water.

The solubility in 1% SDS in water after 24 hours rotation was 0.7 mg/ml for picropodophyllin polymorph B.

The solubility in 1% SDS in water after 24 hours rotation was 0.4 mg/ml for picropodophyllin polymorph C.

Example 6

Dynamic Vapour Sorption (DVS)

The hygroscopicity of the samples was studied by Dynamic Vapor Sorption Gravimetry (DVS) using a DVS-1 (Surface Measurement Ltd., UK).

Approximately 10 mg of substance (i.e. picropodophyllin polymorph B or picropodophyllin polymorph C) was weighed into a glass cup. The relative weight was recorded at 20 second interval, when the target relative humidity (RH) over the sample was increased stepwise from 0% to 90%, and then similarly decreased back to 0% RH, with 10% RH per step. Each sample was run in three consecutive full cycles. The condition to proceed to the next level of RH was a weight increase below or equal to 0.001% within 15 minutes, with a maximum total time per step of 24 hours. The temperature was kept at 25° C.

The DVS experiment resulted in a 0.2% mass increase for picropodophyllin polymorph B and picropodophyllin polymorph C, respectively, from 0 to 90% RH.

Example 7

Thermogravimetric Analysis (TGA)

Picropodophyllin polymorph B and picropodophyllin polymorph C were analysed using thermogravimetry as described hereinafter.

Thermogravimetric analysis (TGA) was performed on a Seiko TG/DTA 6200 and open 90 µl Pt-pans with ca 10 to 25 mg of sample and a nitrogen flow of 200 ml/min. The temperature program was ambient (20° C.) to 400° C. with a heating rate of 10° C./min. A blank was subtracted and the TG data was normalized with respect to sample size and analyzed using the Muse Standard Analysis software, version 6.1 U (Seiko, Japan).

For picropodophyllin polymorph B the mass loss from ambient temperature to 150° C. was found to be 0.0±0.1%.

For picropodophyllin polymorph C the mass loss from ambient temperature to 150° C. was found to be 0.1±0.1%.

The TG analysis showed that no hydrate or solvate formation had taken place.

Example 8

Solid State Stability Study

A three month solid state stability study of polymorph B and polymorph C respectively, was performed. Analysis was made by using X-Ray Powder Diffration (XRPD) and Thermogravimetry (TGA).

After storage in open containers during 3 months at 40° C./75% RH and after 3 months storage at 25° C./60% RH respectively, there had been no change in appearance for polymorph B nor for polymorph C since day 0 (i.e. at the initiation time of the study).

X-Ray Powder Diffraction (XRPD)

Experiments were run as described above using Cu $K_{\alpha 1}$ radiation (45 kV and 40 mA) at ambient temperature and humidity. Scans were run in continous scan mode in the range 2-50° 2θ using automatic divergence and antiscatter slits with observed length of 10 mm, a step size of 0.013° 2θ and a common counting time of 97.920 seconds.

Data collections were done with the application software X'Pert Data Collector version 2.2d and instrument control software version 1.9D, and pattern analysis was done X'Pert Data Viewer version 1.2c. All software's come from PANanalytical, Netherlands.

Figure 7:
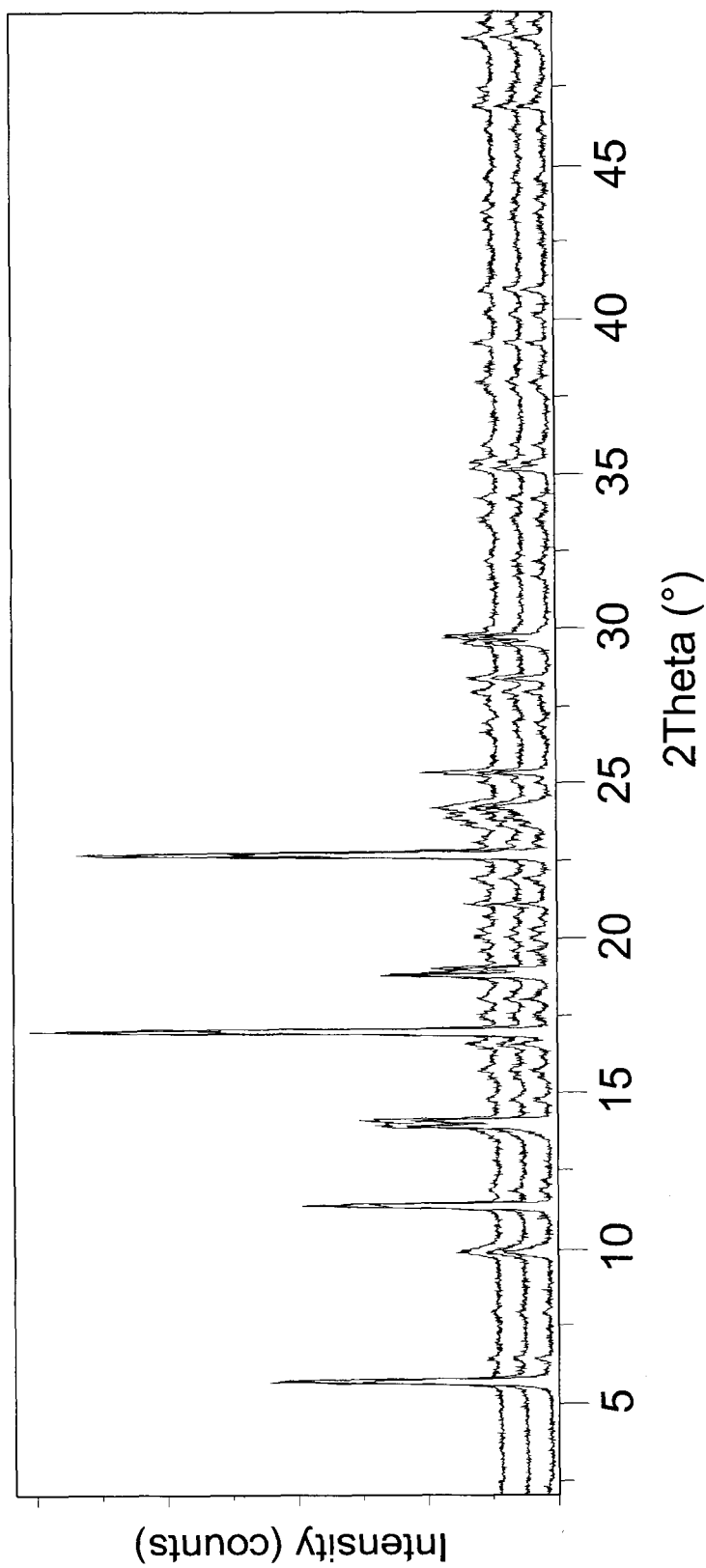
FIG. 7 is an overlaid X-ray powder diffractogram (XRPD) of picropodophyllin polymorph B at the time of initiation of the stability study (bottom), stored 3 months at 25° C./60% RH (middle) and stored 3 months at 40° C./75% RH (top). The XRPD patterns are offset in order improve the visual comparison.

X-ray powder diffraction (XRPD) patterns of the initial analysis, after 3 months storage at 40° C./75% RH and after 3 months storage at 25° C./60% RH of polymorph B is shown in FIG. 7.

Figure 8:
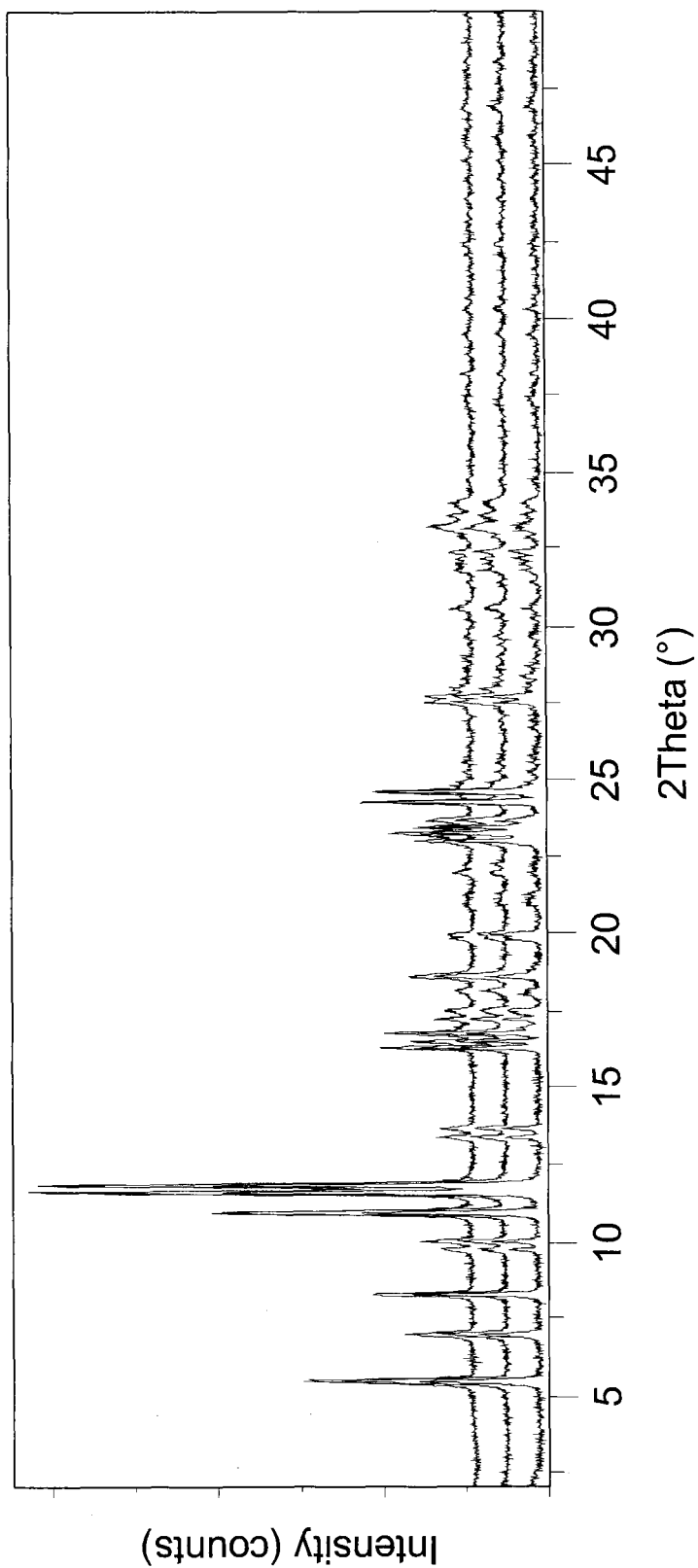
FIG. 8 is an overlaid X-ray powder diffractogram (XRPD) of picropodophyllin polymorph C at the time of initiation of the stability study (bottom), stored 3 months at 25° C./60% RH (middle) and stored 3 months at 40° C./75% RH (top). The XRPD patterns are offset in order improve the visual comparison.

X-ray powder diffraction (XRPD) patterns of the initial analysis, after 3 months storage at 40° C./75% RH and after 3 months storage at 25° C./60% RH of polymorph C is shown in FIG. 8.

Thermogravimetry (TGA)

Thermogravimetry (TGA) was performed on a Seiko TG/DTA 6200 and open 90 µl Pt-pans with ca 10 to 20 mg of sample and a nitrogen flow of 200 mL/min. The temperature program was ambient (20° C.) to 400° C. with a heating rate of 10° C./min. A blank was subtracted and the TG data was normalized with respect to sample size and analyzed using the Muse Standard Analysis software, version 6.1 U.

For picropodophyllin polymorph B the mass loss from ambient temperature to 150° C. was found to be 0.0±0.1% after 3 months storage at 40° C./75% RH.

For picropodophyllin polymorph C the mass loss from ambient temperature to 150° C. was found to be 0.1±0.1% after 3 months storage at 40° C./75% RH.

The performed solid state analysis for polymorph B as well as for polymorph C does not show any sign(s) of solid-state instability after 3 months storage at 25° C./60% RH and 40° C./75% RH, respectively.

Example 9

Dissolution Study

The dissolution rate and apparent solubility of polymorph B and polymorph C in buffer pH 6.5 and fed state simulated intestinal fluid was studied. The wording "apparent solubility" refers to the concentration of polymorph B or polymorph C at apparent equilibrium (supersaturation).

Methods

Phosphate buffer pH 6.5 (PhB 6.5) was prepared according to a protocol by Galia and co-workers (Galia, E., et al. Evaluation of various dissolution media for predicting in vivo performance of class I and II drugs. *Pharm Res* 15, pp. 698-705 (1998)). Briefly, 1000 mL of 150 mM $Na_2HPO_4$ buffer pH 6.5 was prepared by dissolving 3.95 g $Na_2HPO_4xH_2O$, 6.19 g NaCl and 0.42 g NaOH in a volumetric flask by adding purified water. The pH was adjusted to pH to 6.5 by titration with 0.5 M NaOH and the volume was adjusted to 1000 mL with purified water. This buffer was sterile filtered and thereafter stored in refrigerator. Fed state simulated intestinal fluid (FeSSIF pH 6.5) was prepared fresh on the day of the experiment by dissolving 1.12 g of Na-taurocholate/lecithin powder (ePhares, Switzerland) in 100 mL PhB ((Galia, E., et al.

Evaluation of various dissolution media for predicting in vivo performance of class I and II drugs. *Pharm Res* 15, pp. 698-705 (1998)). The media was stirred and preheated to 37±1° C. resulting in clear solution of pH 6.5 which contained a mixed micelle system of 15 mM taurocholate and 3.75 mM lecithin.

Dissolution Profiling—Powder Experiments

Dissolution rate and apparent solubility was measured with the pDISS Profiler™ (pION INC, MA, USA) from 0.3-1.3 mg compound weighed into the vial to which the preheated (37° C.) dissolution medium was added. In each experiment, dissolution rate and solubility were investigated in 15 mL solvent at 37±1° C. using a stirring rate of 100 rpm. Each UV probe was calibrated with its own standard curve prior to the experiment. The obtained results were analysed with the software accompanying the pDISS equipment.

The detailed procedure of the powder dissolution experiments, including the theoretical background, can be found in Avdeef, A., Tsinman, K., Tsinman, O., Sun, N. & Voloboy, D. Miniaturization of powder dissolution measurement and estimation of particle size. *Chem Biodivers* 6, 1796-1811 (2009); in Fagerberg, J. H., et al. Dissolution Rate and Apparent Solubility of Poorly Soluble Drugs in Biorelevant Dissolution Media. *Mol Pharm* 7, 1419-1430, (2010); and in Tsinman, K., Avdeef, A., Tsinman, O. & Voloboy, D. Powder dissolution method for estimating rotating disk intrinsic dissolution rates of low solubility drugs. *Pharm Res* 26, 2093-2100 (2009).

Intrinsic dissolution rates (IDR) and apparent solubility of polymorph B and polymorph C respectively in PhB 6.5 and FeSSIF are shown in Table 1 and Table 2, respectively.

It was shown that the data obtained was consistent also when repeating the analyses and extending the time frame for the assay from <2 hours to up to 29 hours.

The effect of naturally available intestinal lipids was investigated by the FeSSIF dissolution profile. The polymorphs displayed the following solubility increase in FeSSIF as compared to PhB 6.5: Picropodophyllin polymorph B: 2.2-fold, and Picropodophyllin polymorph C, 2.2-fold higher solubility in FeSSIF.

The invention claimed is:

1. Picropodophyllin polymorph C having an X-ray powder diffraction pattern exhibiting peaks at 5.5, 7.0, 8.3, 11.0, 11.6 and 11.8±0.2° 2θ.

2. Picropodophyllin polymorph C according to claim 1, wherein the polymorph exhibits a peak at 5.4±0.2° 2θ.

3. Picropodophyllin polymorph C according to claim 2, wherein the polymorph exhibits peaks at 5.4 and 6.9±0.2° 2θ.

4. Picropodophyllin polymorph C according to claim 2, wherein the polymorph exhibits peaks at 5.4, 6.9, 8.2, 9.7, 10.0, 10.9, 11.5 and 11.7±0.2° 2θ.

5. Picropodophyllin polymorph C exhibiting an X-ray powder diffraction pattern as shown in FIG. 3.

6. Picropodophyllin polymorph C exhibiting an X-ray powder diffraction pattern as shown in FIG. 4.

7. Picropodophyllin polymorph C according to claim 6, wherein the polymorph has an IR spectrum exhibiting a peak at 1773.8 cm$^{-1}$.

8. Picropodophyllin polymorph C according to claim 7, wherein the polymorph has an IR spectrum exhibiting peaks at 1031.2; 1129.0; 1184.5; 1233.6; 1425.8; 1462.5; 1479.0; 1592.8; 1773.8; 2842.2; 2943.2; 2993.8; and 3436.0 cm$^{-1}$.

9. Picropodophyllin polymorph C according to claim 5, wherein the polymorph has an IR spectrum exhibiting a peak at 1773.8 cm$^{-1}$.

TABLE 1

Results for picropdophyllin polymorph B and picropdophyllin polymorph C in PhB 6.5.

| | Apparent Solubility assay 1 [μg/ml] | IDR assay 1 [μg/min/cm$^2$] | Apparent Solubility assay 2 [μg/ml] | IDR assay 2 [μg/min/cm$^2$] | Apparent Solubility Assay 1 + 2 [μg/ml] | IDR assay 1 + 2 [μg/min/cm$^2$] |
|---|---|---|---|---|---|---|
| B | 11.72 ± 0.22 | 1.12 ± 0.02 | n.d. | n.d. | n.d | n.d |
| C | 5.88 ± 0.09 | 0.57 ± 0.03 | 5.81 ± 0.38 | 0.56 ± 0.05 | 5.85 ± 0.25 | 0.57 ± 0.03 |

Assay times:
Assay 1: Polymorph B: 19 hours; Polymorph C: 1.7 hours.
Assay 2: Picropdophyllin polymorph C: 29 hours (reported value is obtained after 50 minutes due to that the compound over time was sticking to the probes and severely affected the readings, but was not considered to affect the values).
Values are reported as mean ± standard deviation.
Assay 1 and 2 were performed in triplicates, respectively.
n.d. = Not Determined.

TABLE 2

Results for picropdophyllin polymorph B and picropdophyllin polymorph C in FeSSIF pH 6.5.

| | Apparent Solubility assay 1 [μg/ml] | IDR assay 1 [μg/min/cm$^2$] | Apparent Solubility assay 2 [μg/ml] | IDR assay 2 [μg/min/cm$^2$] | Apparent Solubility Assay 1 + 2 [μg/ml] | IDR assay 1 + 2 [μg/min/cm$^2$] |
|---|---|---|---|---|---|---|
| B | 25.51 ± 0.51 | 2.45 ± 0.05 | n.d. | n.d. | n.d | n.d |
| C | 12.94 ± 0.17 | 1.24 ± 0.02 | 12.21 ± 1.07 | 1.29 ± 0.09 | 12.58 ± 0.80 | 1.23 ± 0.11 |

Assay times:
Assay 1: Picropdophyllin polymorph B: 16 hours; Picropdophyllin Polymorph C: 1.3 hours.
Assay 2: Picropdophyllin Polymorph C: 25 hours. Assay 1 and 2 were performed in triplicates, respectively.
n.d. = Not Determined.

10. Picropodophyllin polymorph C according to claim 9, wherein the polymorph has an IR spectrum exhibiting peaks at 1031.2; 1129.0; 1184.5; 1233.6; 1425.8; 1462.5; 1479.0; 1592.8; 1773.8; 2842.2; 2943.2; 2993.8; and 3436.0 cm$^{-1}$.

11. Picropodophyllin polymorph C according to claim 1, wherein the polymorph exhibits an IR spectrum as shown in FIG. 6.

12. Picropodophyllin polymorph C according to claim 1, wherein the picropodophyllin polymorph C contains less than 10% of any other polymorph and/or other crystal and non-crystal forms of picropodophyllin.

13. A pharmaceutical composition comprising picropodophyllin polymorph C according to claim 1, in admixture with a pharmaceutically and pharmacologically acceptable adjuvant, diluent and/or carrier.

14. A kit of comprising:
(i) picropodophyllin polymorph C according to claim 1; and
(ii) an anti-cancer compound;
for sequential or simultaneous administration.

15. A method for the treatment of cancer, whereby a therapeutically effective amount of picropodophyllin polymorph C according to claim 1 is administered to a patient in need of such treatment, wherein said cancer is any one of lung cancer; breast cancer; head and neck cancer; gastrointestinal cancer; genito-urinary cancer; gynecologic cancer; hematologic cancer; musculoskeletal cancer; skin cancer; brain cancer; neurologic cancer; endocrine cancer; or eye cancer.

16. The method according to claim 15, wherein said cancer is non-small cell lung carcinoma (NSCLC).

17. The method according to claim 16, wherein the non-small cell lung carcinoma (NSCLC) is adenocarcinoma, squamous cell carcinoma or large-cell lung carcinoma.

18. The method according to claim 15, wherein said cancer is any one selected from small cell lung cancer; oral cancer; sinusoidal cancer; pharyngeal cancer; oesophageal cancer; stomach cancer; colon cancer; rectal cancer; gastrointestinal stromal tumor; liver cancer; pancreatic cancer; prostate cancer; bladder cancer; kidney cancer; ovarian cancer; cervical cancer; endometric cancer; uterine sarcoma; myeloid leukemia; lymphocytic leukemia; lymphomas; multiple myeloma; Ewing's sarcoma; osteosarcoma; soft tissue sarcoma; malignant melanoma; basal cell cancer; squamous cell cancer; Kaposi's sarcoma; glioma; glioblastoma; astrocytoma; medulloblastoma; craniopharyngeoma; neuroblastoma; adrenocortical cancer; paraganglioma; pheochromocytoma; thyroid cancer; retinoblastoma; and uveal melanoma.

19. A method for the preparation of picropodophyllin polymorph C according to claim 1, whereby picropodophyllin is recrystallized from a solvent selected from the group consisting of propionitrile, methyl ethyl ketone, n-butyl acetate, isobutylnitrile, butylformate, n-butylformate, iso-butylformate, tert-butylformate, dipropyl carbonate, and any combination of these solvents.

20. A method for transforming a picropodophyllin polymorph B into a picropodophyllin polymorph C according to any one of claims 1-11, comprising the steps of:
a) mixing the picropodophyllin polymorph B with the picropodophyllin polymorph C in a saturated solution of picropodophyllin in an organic solvent;
b) stirring the mixture obtained in step a) to obtain a precipitate; and
c) filtering off the thus obtained precipitate.

* * * * *